United States Patent
Ullrich et al.

(10) Patent No.: US 9,579,143 B2
(45) Date of Patent: Feb. 28, 2017

(54) ELECTROSURGICAL TOOL HAVING TACTILE FEEDBACK

(75) Inventors: Christopher Ullrich, Ventura, CA (US); Pedro Gregorio, Verdun (CA)

(73) Assignee: Immersion Corporation, San Jose, CA (US)

( * ) Notice: Subject to any disclaimer, the term of this patent is extended or adjusted under 35 U.S.C. 154(b) by 970 days.

(21) Appl. No.: 13/206,955

(22) Filed: Aug. 10, 2011

(65) Prior Publication Data
US 2012/0041436 A1 Feb. 16, 2012

Related U.S. Application Data

(60) Provisional application No. 61/373,009, filed on Aug. 12, 2010.

(51) Int. Cl.
*A61B 18/12* (2006.01)
*A61B 18/14* (2006.01)
*A61B 18/00* (2006.01)

(52) U.S. Cl.
CPC .............. *A61B 18/12* (2013.01); *A61B 34/76* (2016.02); *A61B 18/1206* (2013.01); *A61B 18/1442* (2013.01); *A61B 2018/00303* (2013.01); *A61B 2018/00684* (2013.01); *A61B 2018/00875* (2013.01)

(58) Field of Classification Search
CPC ................ A61B 18/12; A61B 18/1442; A61B 2018/00875; A61B 2019/2292
USPC ............................................... 606/37, 34, 41
See application file for complete search history.

(56) References Cited

U.S. PATENT DOCUMENTS

| | | | |
|---|---|---|---|
| 3,785,381 A | 1/1974 | Lower et al. |
| 3,950,984 A | 4/1976 | Russel |
| 4,407,686 A | 10/1983 | Cook et al. |
| 4,608,861 A | 9/1986 | Wachtler et al. |
| 4,841,987 A | 6/1989 | Brown et al. |
| 4,858,611 A | 8/1989 | Elliott |
| 5,047,046 A | 9/1991 | Bodoia |

(Continued)

FOREIGN PATENT DOCUMENTS

| | | |
|---|---|---|
| CA | 2520942 | 3/2007 |
| DE | 4213426 | 10/1992 |

(Continued)

OTHER PUBLICATIONS

EP Appl. No. 11 17 6993, Extended European Search Report, dated Nov. 8, 2011.

(Continued)

*Primary Examiner* — Daniel Fowler
(74) *Attorney, Agent, or Firm* — Medler Ferro Woodhouse & Mills

(57) ABSTRACT

A surgical tool system including a laparoscopic surgical tool for heating, ablating, sealing, and/or dissecting tissue, a control system for monitoring impedance of the tissue during treatment thereof, and a tactile feedback system integrated onto a handle of the tool that generates relevant feedback from the control system in at least the form of haptic effects to the user. The tactile feedback alerts the tool user of changes in tissue properties, i.e., when the impedance of the tissue indicates that the treatment procedure is complete. In addition, the tactile feedback provided may supply information relating to the operating status of the control system to the user.

18 Claims, 4 Drawing Sheets

(56) References Cited

U.S. PATENT DOCUMENTS

| | | | |
|---|---|---|---|
| 5,188,111 A | 2/1993 | Yates et al. | |
| 5,339,799 A | 8/1994 | Kami et al. | |
| 5,357,956 A | 10/1994 | Nardella | |
| 5,389,849 A | 2/1995 | Asano et al. | |
| 5,403,312 A * | 4/1995 | Yates et al. | 606/50 |
| 5,411,511 A | 5/1995 | Hall | |
| 5,503,320 A | 4/1996 | Webster et al. | |
| 5,529,235 A | 6/1996 | Boiarski et al. | |
| 5,609,607 A | 3/1997 | Hechtenberg et al. | |
| 5,623,582 A | 4/1997 | Rosenberg | |
| 5,649,934 A | 7/1997 | Smeltzer, III et al. | |
| 5,685,474 A | 11/1997 | Seeber | |
| 5,688,270 A | 11/1997 | Yates et al. | |
| 5,713,896 A | 2/1998 | Nardella | |
| 5,728,044 A | 3/1998 | Shan | |
| 5,733,281 A | 3/1998 | Nardella | |
| 5,767,840 A | 6/1998 | Selker | |
| 5,771,902 A | 6/1998 | Lee et al. | |
| 5,810,880 A | 9/1998 | Jensen et al. | |
| 5,833,634 A | 11/1998 | Laird et al. | |
| 5,836,894 A | 11/1998 | Sarvazyan | |
| 5,928,158 A | 7/1999 | Aristides | |
| 5,928,159 A | 7/1999 | Eggers et al. | |
| 5,950,629 A | 9/1999 | Taylor et al. | |
| 5,965,880 A | 10/1999 | Wolf et al. | |
| 5,989,199 A | 11/1999 | Cundari et al. | |
| 6,004,335 A | 12/1999 | Kaitekunas et al. | |
| 6,024,741 A | 2/2000 | Williamson et al. | |
| 6,063,031 A | 5/2000 | Cundari et al. | |
| 6,096,004 A | 8/2000 | Meglan et al. | |
| 6,132,441 A | 10/2000 | Grace | |
| 6,190,334 B1 | 2/2001 | Lasky et al. | |
| 6,267,761 B1 | 7/2001 | Ryan | |
| 6,354,147 B1 | 3/2002 | Gysling et al. | |
| 6,375,471 B1 | 4/2002 | Wendlandt et al. | |
| 6,423,057 B1 | 7/2002 | He et al. | |
| 6,436,107 B1 | 8/2002 | Wang et al. | |
| 6,451,015 B1 | 9/2002 | Rittman, III et al. | |
| 6,494,882 B1 | 12/2002 | Lebouitz et al. | |
| 6,520,185 B1 * | 2/2003 | Bommannan et al. | 128/898 |
| 6,594,552 B1 | 7/2003 | Nowlin et al. | |
| 6,690,963 B2 | 2/2004 | Ben-Haim et al. | |
| 6,718,196 B1 | 4/2004 | Mah et al. | |
| 6,730,021 B2 | 5/2004 | Vassiliades, Jr. et al. | |
| 6,810,281 B2 | 10/2004 | Brock et al. | |
| 6,817,973 B2 | 11/2004 | Merril et al. | |
| 6,945,981 B2 | 9/2005 | Donofrio et al. | |
| 6,969,384 B2 | 11/2005 | de Juan, Jr. et al. | |
| 7,108,695 B2 | 9/2006 | Witt et al. | |
| 7,118,582 B1 | 10/2006 | Wang et al. | |
| 7,122,028 B2 | 10/2006 | Looper et al. | |
| 7,126,303 B2 | 10/2006 | Farritor et al. | |
| 7,200,445 B1 | 4/2007 | Dalbec et al. | |
| 7,206,627 B2 | 4/2007 | Abovitz et al. | |
| 7,270,664 B2 | 9/2007 | Johnson et al. | |
| 7,280,863 B2 | 10/2007 | Shachar | |
| 7,300,450 B2 | 11/2007 | Vleugels et al. | |
| 7,366,562 B2 | 4/2008 | Dukesherer et al. | |
| 7,373,219 B2 | 5/2008 | Nowlin et al. | |
| 7,393,354 B2 | 7/2008 | Buchman et al. | |
| 7,422,139 B2 | 9/2008 | Shelton, IV et al. | |
| 7,720,532 B2 | 5/2010 | Hashimshony et al. | |
| 7,771,424 B2 | 8/2010 | McGaffigan | |
| 7,963,192 B2 | 6/2011 | Mayenberger et al. | |
| 8,216,212 B2 | 7/2012 | Grant et al. | |
| 2001/0004700 A1 | 6/2001 | Honeycutt et al. | |
| 2001/0025150 A1 | 9/2001 | de Juan, Jr. et al. | |
| 2002/0112547 A1 | 8/2002 | Eltaib et al. | |
| 2002/0120188 A1 | 8/2002 | Brock et al. | |
| 2003/0023250 A1 | 1/2003 | Watschke et al. | |
| 2003/0057973 A1 | 3/2003 | Nojima et al. | |
| 2004/0009459 A1 | 1/2004 | Anderson et al. | |
| 2004/0019447 A1 | 1/2004 | Shachar | |
| 2004/0039429 A1 | 2/2004 | Daniel et al. | |
| 2004/0106916 A1 | 6/2004 | Quaid et al. | |
| 2004/0167559 A1 | 8/2004 | Taylor et al. | |
| 2004/0249268 A1 | 12/2004 | Da Silva | |
| 2005/0021024 A1 | 1/2005 | Hooven | |
| 2005/0090815 A1 | 4/2005 | Francischelli et al. | |
| 2005/0131390 A1 | 6/2005 | Heinrich et al. | |
| 2005/0223327 A1 | 10/2005 | Cunningham et al. | |
| 2005/0245910 A1 | 11/2005 | Wright et al. | |
| 2006/0030845 A1 | 2/2006 | Leung et al. | |
| 2006/0033703 A1 | 2/2006 | Olien et al. | |
| 2006/0095033 A1 | 5/2006 | Garabedian et al. | |
| 2006/0106375 A1 * | 5/2006 | Werneth et al. | 606/32 |
| 2006/0142657 A1 | 6/2006 | Quaid et al. | |
| 2006/0206031 A1 | 9/2006 | Hasegawa | |
| 2006/0207978 A1 | 9/2006 | Rizun et al. | |
| 2006/0224219 A1 * | 10/2006 | Podhajsky et al. | 607/96 |
| 2006/0264755 A1 | 11/2006 | Maltz et al. | |
| 2006/0278680 A1 | 12/2006 | Viola et al. | |
| 2006/0279534 A1 | 12/2006 | Powers et al. | |
| 2006/0293643 A1 | 12/2006 | Wallace et al. | |
| 2007/0018958 A1 | 1/2007 | Tavakoli et al. | |
| 2007/0043352 A1 | 2/2007 | Garrison et al. | |
| 2007/0055173 A1 * | 3/2007 | DeLonzor et al. | 600/564 |
| 2007/0062547 A1 | 3/2007 | Pappone | |
| 2007/0073282 A1 | 3/2007 | McGaffigan et al. | |
| 2007/0112284 A1 | 5/2007 | Hoffman et al. | |
| 2007/0135735 A1 | 6/2007 | Ellis et al. | |
| 2007/0142749 A1 | 6/2007 | Khatib et al. | |
| 2007/0167940 A1 * | 7/2007 | Stevens-Wright | 606/32 |
| 2007/0175953 A1 | 8/2007 | Shelton, IV et al. | |
| 2007/0175962 A1 | 8/2007 | Shelton, IV et al. | |
| 2007/0175964 A1 | 8/2007 | Shelton et al. | |
| 2007/0270884 A1 | 11/2007 | Smith et al. | |
| 2007/0278277 A1 | 12/2007 | Wixey et al. | |
| 2007/0279401 A1 | 12/2007 | Ramstein et al. | |
| 2008/0009747 A1 | 1/2008 | Saadat et al. | |
| 2008/0086120 A1 | 4/2008 | Mirza et al. | |
| 2008/0117166 A1 | 5/2008 | Rosenberg | |
| 2008/0161796 A1 | 7/2008 | Cao et al. | |
| 2008/0167662 A1 | 7/2008 | Kurtz | |
| 2008/0167672 A1 | 7/2008 | Giordano et al. | |
| 2008/0197167 A1 | 8/2008 | Viola et al. | |
| 2008/0200861 A1 * | 8/2008 | Shalev et al. | 604/20 |
| 2008/0251568 A1 | 10/2008 | Zemlok et al. | |
| 2008/0251569 A1 | 10/2008 | Smith et al. | |
| 2008/0275465 A1 * | 11/2008 | Paul | A61B 18/1492 606/129 |
| 2009/0090763 A1 | 4/2009 | Zemlok et al. | |
| 2009/0157071 A1 * | 6/2009 | Wham et al. | 606/33 |
| 2009/0163904 A1 | 6/2009 | Miller et al. | |
| 2010/0065609 A1 | 3/2010 | Schwemberger | |
| 2010/0179423 A1 | 7/2010 | Ramstein et al. | |
| 2011/0046659 A1 | 2/2011 | Ramstein et al. | |
| 2011/0062211 A1 | 3/2011 | Ross et al. | |
| 2011/0118779 A1 | 5/2011 | Olien et al. | |
| 2011/0288573 A1 | 11/2011 | Yates et al. | |
| 2012/0116379 A1 | 5/2012 | Yates et al. | |
| 2012/0138658 A1 | 6/2012 | Ullrich et al. | |
| 2012/0143182 A1 | 6/2012 | Ullrich | |

FOREIGN PATENT DOCUMENTS

| | | |
|---|---|---|
| EP | 1 254 637 | 11/2002 |
| EP | 1 852 078 | 11/2007 |
| EP | 2 044 890 | 4/2009 |
| EP | 2 218 409 | 8/2010 |
| EP | 2 277 458 | 1/2011 |
| EP | 2 283 781 | 2/2011 |
| EP | 2 417 925 | 2/2012 |
| JP | 2005-021703 | 1/2005 |
| JP | 2008-036441 | 2/2008 |
| JP | 2009-045429 | 3/2009 |
| JP | 2009-189833 | 8/2009 |
| JP | 2009-247887 | 10/2009 |
| JP | 2010-046425 | 3/2010 |
| WO | WO 94/24949 | 11/1994 |
| WO | WO 03/020139 | 3/2003 |
| WO | WO 03/090630 | 11/2003 |
| WO | WO 2004/067053 | 8/2004 |
| WO | WO 2005/013803 | 2/2005 |

(56) References Cited

FOREIGN PATENT DOCUMENTS

| WO | WO 2005/110304 | 11/2005 |
|---|---|---|
| WO | WO-2007/067628 | 6/2007 |
| WO | WO 2008/033937 | 3/2008 |
| WO | WO-2009/009220 | 1/2009 |
| WO | 2009/143092 | 11/2009 |
| WO | WO-2010/008663 | 1/2010 |
| WO | 2010/042786 | 4/2010 |
| WO | WO-2010/065314 | 6/2010 |
| WO | WO-2010/083060 | 7/2010 |
| WO | 2010/109932 | 9/2010 |

OTHER PUBLICATIONS

EP Appl. No. 11 19 1549, Extended European Search Report, dated Feb. 22, 2012.

"Tactile Sensor Acts as a Human Finger in Minimally Invasive Surgery", www.physorg.com/news102155952.html, 2007.

Bethea, et al., Abstract of: "Application of Haptic Feedback to Robotic Surgery", http://www.liebertonline.com/doi/abs/10.1089/1092642041255441, Downloaded: Nov. 25, 2008.

Bholat, et al., Abstract of: "Tactile Feedback is Present During Minimally Invasive Surgery", J Am Coll Surg, Oct. 1999, 189(4), pp. 349-355; http://www.ncbi.nlm.nih.gov/pubmed/10509459, Downloaded: Nov. 25, 2008.

Hannaford, et al., "Computerized Endoscopic Surgical Grasper", Proceedings, Medicine Meets Virtual Reality, San Diego, CA, Jan. 1998.

Hu, et al., "Real-Time Haptic Feedback in Laparoscopic Tools for Use in Gastro-Intestinal Surgery", T. Dohi and R. Kikinis (Eds.): MICCAI 2002, LNCS 2488, (2002), pp. 66-74.

Marvik, et al., Abstract of: "Ergonomic Design Criteria for a Novel Laparoscopic Tool Handle with Tactile Feedback", Minerva Chirurgica ISSN 0026-4733, vol. 61, No. 5, (2006), pp. 435-444.

Moy, et al., Abstract of: "A Compliant Tactile Display for Teletaction", http://ieeexplore.ieee.org/xpl/freeabs_all.jsp?tp=&arnumber=845247&isnumber=18314, Downloaded: Nov. 25, 2008.

Okamura, et al., "The Haptic Scissors: Cutting in Virtual Environments", Proceedings of the 2003 IEEE International Conference on Robotics & Automation, Taipei, Taiwan, Sep. 14-19, 2003.

Schirmbeck, et al., "Tactile Feedback without Direct Touch: An Achievement for Robotically Working Heart Surgeons?", nereja.free.fr/files/BMT2005Haptic1.pdf, Downloaded: Nov. 25, 2008.

Yao, et al., "A Tactile Enhancement Instrument for Minimally Invasive Surgery", Computer Aided Surgery, vol. 10, No. 4, pp. 233-239, MICCAI (2004), pp. 89-96.

Notification of Reasons for Refusal (First Office Action—Machine Translation), JP Appl. No. 2011-267623, Oct. 22, 2015.

Notification of Reasons for Refusal (First Office Action—Machine Translation), JP Appl. No. 2011-267665, Sep. 29, 2015.

\* cited by examiner

ELECTROSURGICAL TOOL HAVING TACTILE FEEDBACK

CROSS-REFERENCE TO RELATED APPLICATION

This application claims the benefit of U.S. Appl. No. 61/373,009 filed Aug. 12, 2010, which is hereby incorporated by reference in its entirety.

FIELD OF THE INVENTION

Embodiments hereof relate to surgical tools for treating tissue, wherein information related to the tissue treatment is processed and displayed to a user in one or more feedback modes integrated onto a handle of the tool.

BACKGROUND OF THE INVENTION

As opposed to open surgery in which a surgeon cuts a relatively large incision in the skin of a patient for accessing internal organs, minimally invasive surgical procedures are performed by making relatively small incisions and then inserting tools through the incisions to access the organs. Minimally invasive surgery usually results in shorter hospitalization times, reduced therapy requirements, less pain, less scarring, and fewer complications.

Although minimally invasive surgical procedures involving small incisions include many advantages over open surgery, minimally invasive surgery can still create challenges to a surgeon. For example, the surgeon must typically rely on a miniature camera introduced through an incision to view the patient's internal organs and see how the movement and operation of the tools affects the organs. The camera transmits images to a visual display, allowing the surgeon to see the internal organs and tissues and to see the effect of other minimally invasive tools on the organs and tissues. In this way, the surgeon is able to perform laparoscopic surgery, dissection, cauterization, endoscopy, telesurgery, and the like.

Compared to open surgery, however, minimally invasive surgery presents limitations in visual and haptic perceptions, and creates challenges unique to this type of surgery. One of the major concerns is the potential for tissue damage, possibly caused by inappropriate use of force or excessive application of energy/heat. For example, electrosurgical tools operate by stimulating tissue with a high frequency electric current. The frequency of the current controls the action of the tool, which can include heating, ablating/cauterizing, sealing, and/or dissecting. In a minimally invasive procedure, surgeons must rely on experience and indirect visualization to determine when the tissue is dissected, sealed, ablated or when other changes have occurred in the tissue. Based on the foregoing, there is a need for improved minimally invasive surgical tools and in particular, there is a need for minimally invasive surgical tools having improved feedback related to the surgical procedure.

BRIEF DESCRIPTION OF DRAWINGS

The foregoing and other features and advantages of the invention will be apparent from the following description of embodiments hereof as illustrated in the accompanying drawings. The accompanying drawings, which are incorporated herein and form a part of the specification, further serve to explain the principles of the invention and to enable a person skilled in the pertinent art to make and use the invention. The drawings are not to scale.

DETAILED DESCRIPTION OF THE INVENTION

Specific embodiments of the present invention are now described with reference to the figures, wherein like reference numbers indicate identical or functionally similar elements. The terms "distal" and "proximal" are used in the following description with respect to a position or direction relative to the treating clinician. "Distal" or "distally" are a position distant from or in a direction away from the clinician. "Proximal" and "proximally" are a position near or in a direction toward the clinician.

The following detailed description is merely exemplary in nature and is not intended to limit the invention or the application and uses of the invention. Furthermore, there is no intention to be bound by any expressed or implied theory presented in the preceding technical field, background, brief summary or the following detailed description.

Embodiments hereof relate to a surgical tool system 101 that includes a laparoscopic surgical tool 100 for heating, ablating/cauterizing, sealing, and/or dissecting tissue, a control system 112 for monitoring impedance of the tissue during treatment thereof, and a tactile feedback system 120 integrated into tool 100 that generates relevant feedback from control system 112 in at least the form of haptic effects to the user. The tactile feedback provided by feedback system 120 alerts the tool user of changes in tissue properties, i.e., when impedance of the tissue indicates that the treatment procedure is complete. In addition, as will be explained in more detail herein, the tactile feedback provided by feedback system 120 may supply information relating to the operating status of control system 112 to the user.

Figure 1:
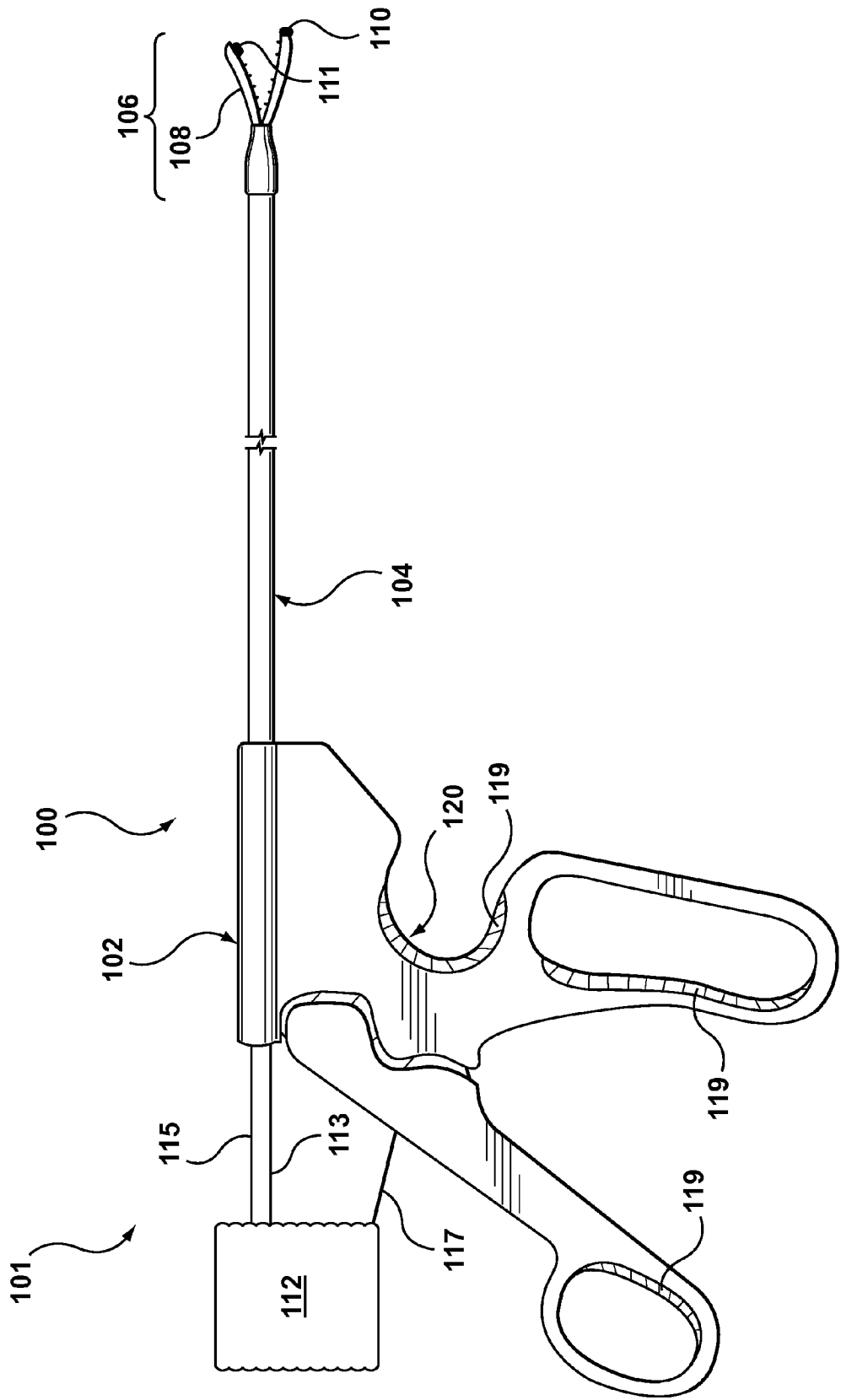
FIG. 1 is a diagram illustrating a side view of a surgical tool system including a laparoscopic surgical tool and an external control system according to an embodiment hereof.

FIG. 1 illustrates an embodiment of an exemplary surgical tool system 101. In this embodiment, surgical tool 100 is shown as a laparoscopic tool which is configured to be inserted through trocar or other minimally invasive access port. Surgical tool 100 includes a handle 102, a shaft 104, and a distal portion 106. Distal portion 106 includes a tip 108. As shown, tip 108 is a grasper or gripper. However, it should be understood that distal portion 106 may include any suitable type of tip having any suitable functionality. Laparoscopic tools in general, like tool 100, are typically thin instruments that each have varied functions (e.g., grippers/graspers, scissors, clip appliers, hook cautery, etc.) and that can be introduced by the surgeon into the abdomen or other areas of the body through trocars, which are hollow tubes with a rubber seal to keep $CO_2$ from leaking. Shaft 104 is designed to connect handle 102 to distal portion 106 and to communicate mechanical actions of handle 102 to distal portion 106. More particularly, the motion of handle 102 opens and closes grasper tip 108 through an internal mechanical connector (not shown) that runs from handle 102 to grasper tip 108. According to some examples of the embodiment of FIG. 1, shaft 104 may be about 20 cm to 30 cm in length and tip 108 may be about 10 mm to 15 mm in length. In addition the shaft 104 is typically 5 mm in diameter, although tools with 3 mm, 10 mm and 12 mm diameters are also commonly used. By manipulating handle 102, an operator can insert distal portion 106 into the abdomen of the patient and control tip 108 of distal portion 106.

Figure 3:
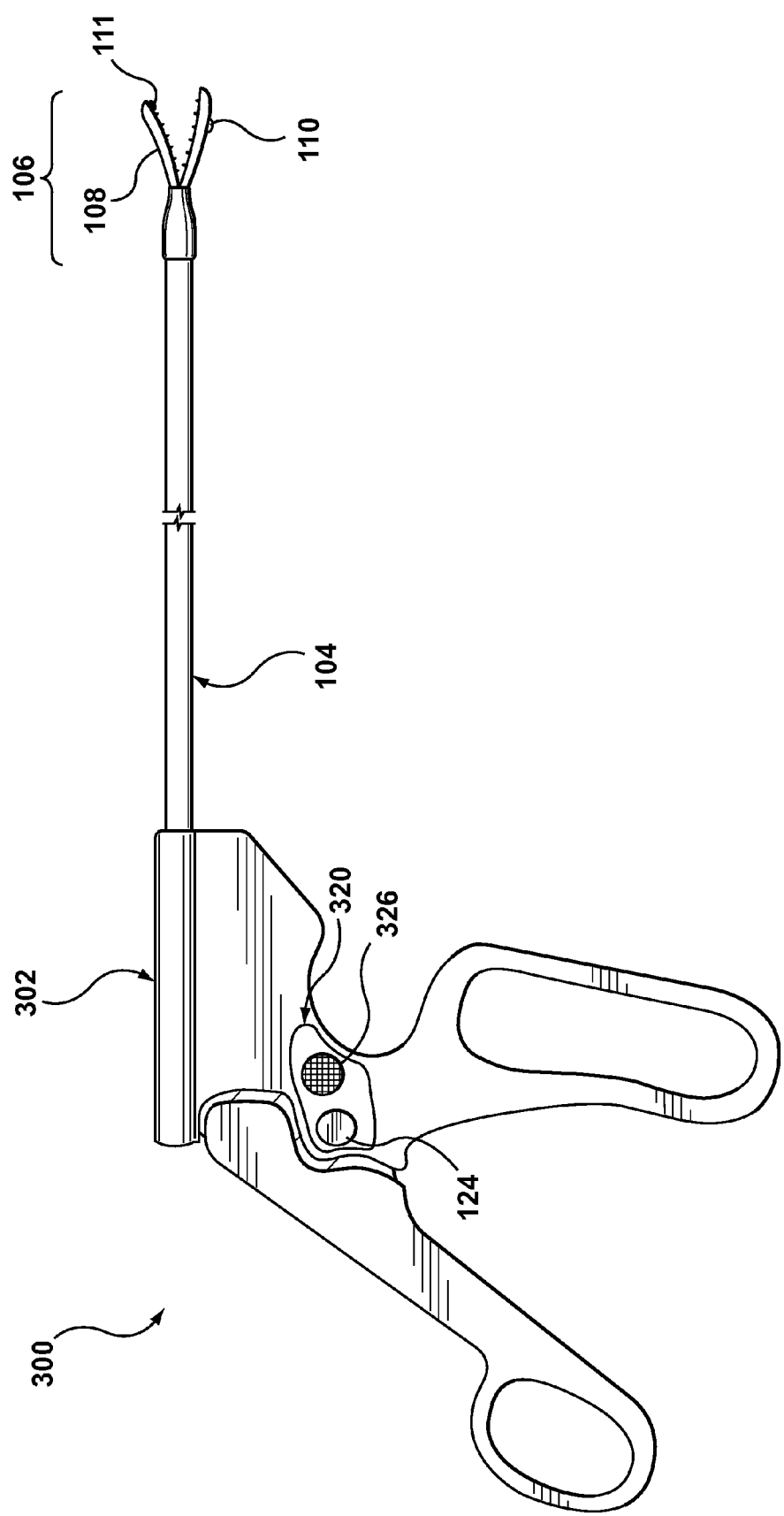
FIG. 3 is a diagram illustrating a side view of a surgical tool system having haptic and audio feedback mechanisms, according to an embodiment hereof.
Figure 4:
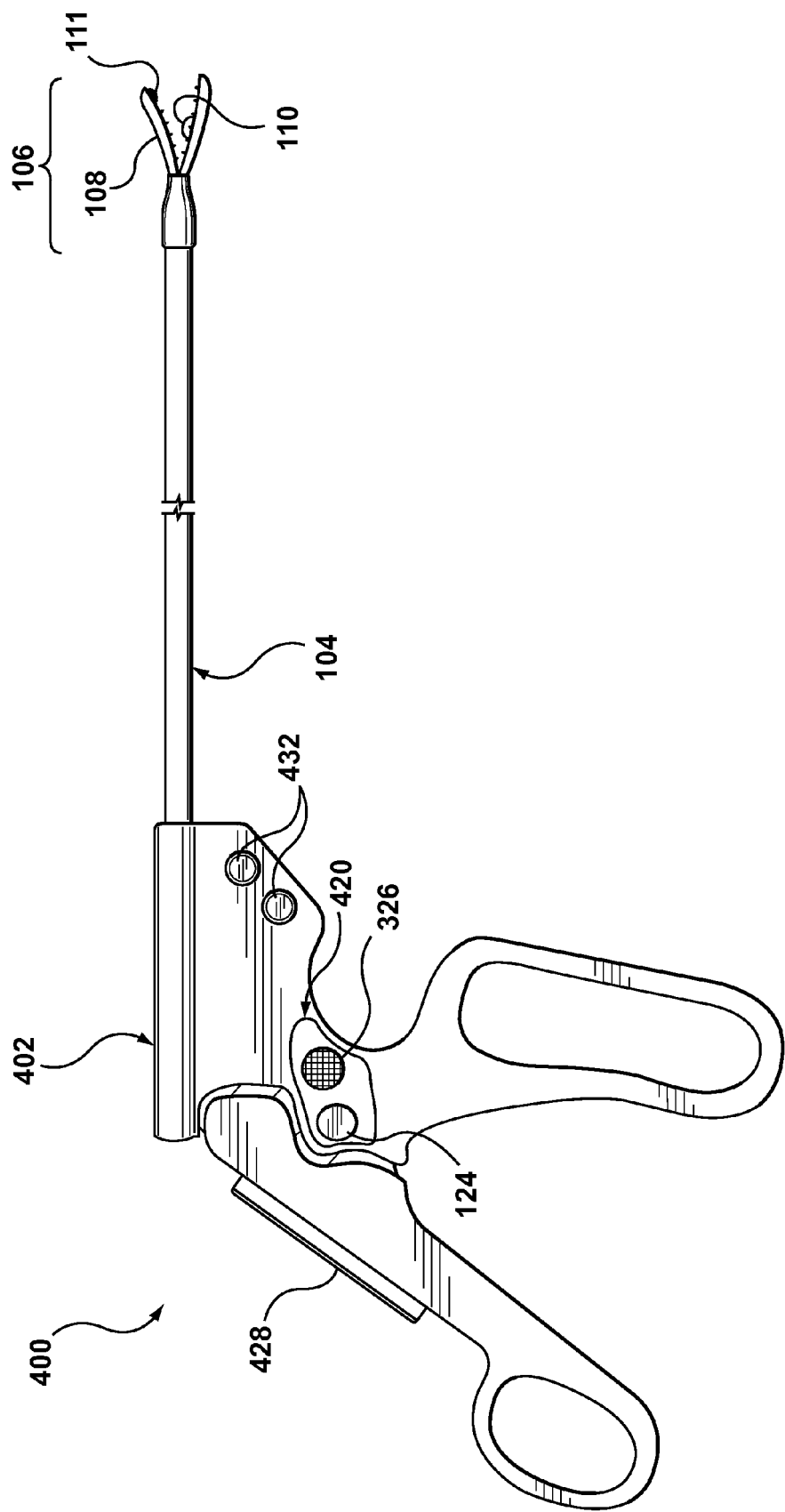
FIG. 4 is a diagram illustrating a side view of a surgical tool system having haptic, audio, and visual feedback mechanisms, according to another embodiment hereof.

Surgical tool 100 includes at least one electrical tissue contact element 110 coupled to and mechanically integrated with tip 108. Tissue contact element 110 is capable of applying heat supplied from a power source 114 of control system 112 to tissue. In one embodiment, tissue contact element 110 is a radiofrequency (RF) electrode for heating, ablating, sealing, and/or dissecting tissue and power source 114 is a radiofrequency (RF) generator. The RF electrode may have any suitable configuration capable of creating an ablative lesion within tissue, including but not limited to a flat electrode, a ring electrode, a hook electrode, or a dome-shaped electrode. Tissue contact element 110 may be coupled to the distal end of the grasper as shown in FIG. 1, to the bottom or outer surface of the grasper as shown in FIG. 3, to an interior surface within jaws of the grasper as shown in FIG. 4, or any other location on the grasper that is deemed appropriate. When distal portion 106 is inserted, the surgeon can manipulate handle 102 to control the location and orientation of tip 108 such that tissue contact element 110 is able to contact certain regions of the patient.

Embodiments hereof are described with respect to an electrosurgical tool having a radiofrequency (RF) electrode for heating, ablating, sealing, and/or dissecting tissue and a radiofrequency (RF) generator for supplying energy thereto. However, it should be understood by those of ordinary skill in the art that power source 114 may generate other types of energy for heating or ablating tissue including electrical energy, ultrasonic energy, cryoablation energy, etc., and in each case, tissue contact element 110 would be a suitable corresponding component to apply the type of energy to tissue. Further, when utilized in conjunction with alternative types of energy, control system 112 may monitor other suitable tissue, system, and/or operating properties rather than impedance to indicate when the treatment procedure is complete.

Surgical tool 100 further includes a common or indifferent reference electrode 111 that is separately disposed from tissue contact element or RF electrode 110. As shown, surgical tool 100 is a bipolar tool and a complete electrical circuit is formed between RF power source 114, electrodes 110 and 111, and the tissue extending between electrodes 110 and 111, with the tissue between electrodes 110 and 111 having an in-circuit impedance that may be monitored to indicate tissue changes as described in more detail herein.

Reference electrode 111 may be coupled to and mechanically integrated with tip 108 at a location spaced apart from RF electrode 110. However, as will be apparent to those of ordinary skill in the art, surgical tool 100 may be a monopolar tool in which the reference electrode is a skin patch electrode or grounding plate positionable outside the patient's body (not shown). In a monopolar embodiment, current and/or voltage flows from power source 114, through tissue contact electrode 110, and into the grounding plate or reference electrode exterior to the patient. As such, although tool 100 is illustrated with only one tissue contact element 110, it will be apparent to those of ordinary skill in the art that multiple tissue contact elements may be coupled to the distal end of tool 100. The same current and/or voltage flows through each tissue contact element and into the grounding plate or reference electrode 111 exterior to the patient.

Electrodes 110, 111 are electrically connected to control system 112 via two electrically conductive leads 113, 115, respectively, that extend through at least one lumen (not shown) of shaft 104. Electrodes 110, 111 may be fixedly attached to the distal ends of the two electrically conductive leads by any suitable means. For example, the electrodes may be attached via welding, soldering, by the use of an electrically conductive adhesive, by the addition of a connecting element there between, or by another mechanical method. Although shown with two leads 113, 115 extending through shaft 104, it will be understood by those of ordinary skill in the art that two leads are only required for bipolar tools having tissue contact element 110 and reference electrode 111 integrated onto distal portion 106 of tool 100. Conversely in a monopolar tool, only one lead is required to run through shaft 104 for connecting control system 112 to one or more tissue contact elements, while an external lead or ground line is connected the grounding plate or reference electrode exterior to the patient.

Figure 2:
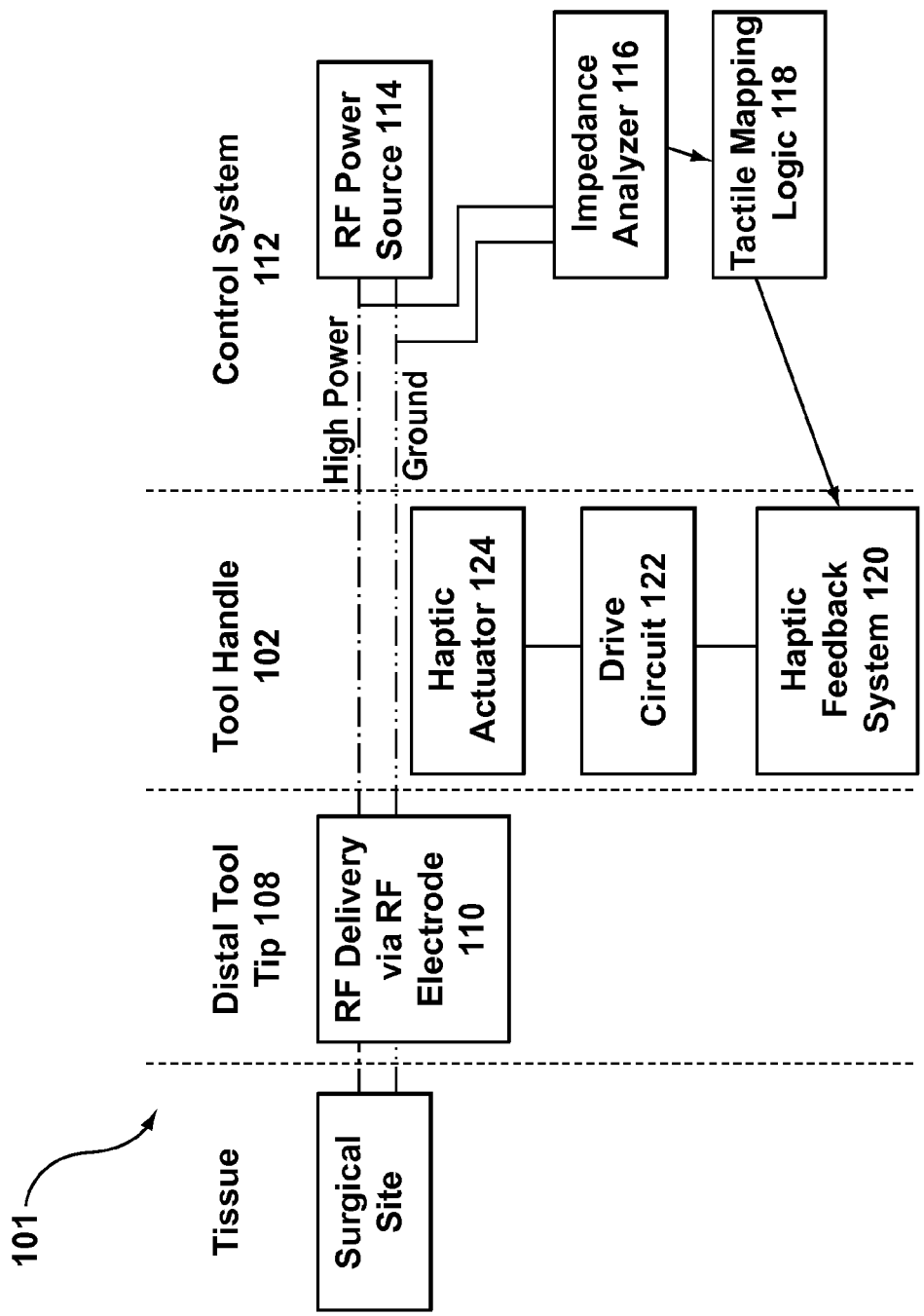
FIG. 2 is a block diagram of the surgical tool system of FIG. 1.

FIG. 2 is a block diagram of surgical tool system 101, further illustrating the relationship between the main components of surgical tool system 101. More particularly, control system 112 includes power source 114, an impedance analyzer 116 for continuously measuring the electrical impedance between RF electrode 110 and reference electrode 111, and a controller or tactile mapping logic 118 configured to process impedance information from impedance analyzer 116 onto tactile feedback signals or commands. The tactile feedback signals are communicated from control system 112 to haptic feedback system 120 on handle 102 of tool 100. Lead 113 electrically connects power supply 114 and RF electrode 110 in order to supply RF power thereto, while lead 115 electrically connects impedance analyzer 116 and reference electrode 111 to communicate impedance measurements between electrodes 110, 111, which preferably include impedance measuring capabilities as will be described in more detail herein. A third lead or tether 117 electrically connects tactile mapping logic 118 to haptic feedback system 120 in handle 102 of tool 100 to control or actuate haptic effects thereto. A fourth lead (not shown) may also be provided between control system 112 and handle 102 to provide an isolated ground line for a low voltage actuator circuit located in handle 102, described in more detail herein.

In one embodiment, power source 114, impedance analyzer 116, and tactile mapping logic 118 are combined into an integral, external component that is separated from surgical tool 100 and is electrically connected to electrodes 110, 111 and haptic feedback system 120 via internal or external wires. Stated in another way, all of the components of control system 112 may be in the same external instrumentation unit. However, in another embodiment, power source 114, impedance analyzer 116, and/or tactile mapping logic 118 may be separate external components that are electrically connected together. In yet another embodiment, one or more of power source 114, impedance analyzer 116, and tactile mapping logic 118 may be mounted within or on handle 102 of surgical tool 100 and are electrically connected to electrodes 110, 111 and haptic feedback system 120 via only internal wires.

Power source 114 generates a current sufficient to heat, ablate, seal, and/or dissect tissue. The current is alternating current and may be of any suitable power level and frequency to heat, ablate, seal, and/or dissect tissue as desired. In one embodiment, power source 116 may be a RF power generator manufactured by Pfizer Valley Lab of Boulder, Colo., which is capable of providing a high output power between 100 W-200 W. For example, power source 116 may generate 100 W at 50 kHz for ablation, although the frequency and power thereof may be varied during the procedure to allow for ablation, cautery, tissue specificity, etc. In addition, power source 114 generates a harmless electric current through lead 110 to allow for the measurement of impedance, as will be described in further detail below. The current is an alternating current (AC) and the selected alternating frequency may be in the range of 1 kHz to 500 kHz or other suitable frequencies known to those of skill in the art of bioelectric impedance. For example, a current of 2 microamperes at 50 KHz may be used.

Power source 114 and impedance analyzer 116 work together in order to continuously measure impedance of the target tissue in real time. Real-time impedance measurement permits the user to gauge the completeness, i.e., degree of transmurality, of the heat, ablation, sealing, or dissection treatment. Specifically, ablation aims to kill cells at an ablation site while leaving the basic structure of the tissue intact and a transmural lesion that extends through the thickness of the tissue blocks electrical signals because it is non-conductive scar tissue. The ability of the lesion to block electrical signals may be accurately indicated by monitoring the impedance of tissue, which can be measured simultaneously with the creation of the lesion. Accordingly, impedance may be monitored to indicate when ablation is complete and transmural. Monitoring impedance at or adjacent to the ablation site and determining completeness of the treatment can be determined according to any criteria. For example, the detection of a particular value of electrical impedance is disclosed in U.S. Pat. No. 5,540,681 to Struhl, et al.; the detection of a desired drop in electrical impedance at the electrode site as an indicator of transmurality is disclosed in U.S. Pat. No. 5,562,721 to Marchlinski et al; the detection of an impedance rise or an impedance rise following an impedance fall are disclosed in U.S. Pat. No. 5,558,671 issued to Yates and U.S. Pat. No. 5,540,684 issued to Hassler; the detection of a series of impedance measurements that are relatively constant over a desired period of time or over a defined number of successive impedance measurements or an abrupt rise in impedance as an indicator of transmurality is disclosed in U.S. Pat. Pub. 2005/0090815 to Francischelli et al., the disclosures of which are each hereby incorporated by reference in their entirety.

As tool 100 heats, ablates, seals, or dissects tissue via tissue contact element 110, power source 114 generates an AC current between electrodes 110, 111 via two electrically conductive leads 113, 115 that extend between control system 112 and electrodes 110, 111, respectively. While current is flowing, impedance analyzer 116 measures a corresponding resistance between electrodes 110, 111 via two electrically conductive leads 113, 115. Impedance analyzer 116 then arithmetically converts the resistance to an impedance measurement. In order to measure impedance, impedance analyzer 116 may include logic resources, such as a microprocessor, configured to analyze and store impedance information derived from electrodes 110, 111. For example, impedance analyzer 116 may include a voltage-current converting circuit, an amplifying circuit, an A/D converting circuit, and an impedance arithmetic operation section.

Impedance may thus be measured between the ablation electrodes or alternatively, between additional electrodes (not shown) located adjacent the ablation electrodes as described in U.S. Pat. No. 5,558,671, herein incorporated by reference in its entirety. In yet another embodiment, impedance may be measured between electrodes 110, 111 via impedance analyzer 116 built into the RF generator and in addition, secondary additional sensor(s) may be located adjacent the ablation electrodes for monitoring tissue properties during heating, ablating, sealing, and/or dissecting. Measurements from the secondary sensor(s) may be utilized to reinforce or supplant the impedance measurements produced by impedance analyzer 116.

Control system 112 further includes controller or tactile mapping logic 118 that processes the impedance information derived from electrodes 110, 111 according to specific algorithms and operator selections. Tactile mapping logic 118 may be a general-purpose or specific-purpose processing device or microcontroller. In one embodiment, tactile mapping logic 118 may be associated with a memory device (not shown) for storing data and/or instructions. The memory device can be any type of storage device or computer-readable medium, such as random access memory ("RAM") or read-only memory ("ROM"). The memory device stores logical instructions, commands, and/or code executed by tactile mapping logic 118. The memory device may also be located internal to control system 112, or any combination of internal and external memory. In another embodiment, logical instructions, commands, and/or code can be implemented in hardware and incorporated in tactile mapping logic 118 using discrete logic circuitry, an application specific integrated circuit ("ASIC"), a programmable gate array ("PGA"), a field programmable gate array ("FPGA"), etc., or any combination thereof. In yet another embodiment, logical instructions, commands, and/or code can be implemented in both hardware in tactile mapping logic 118 and software/firmware stored in the memory.

Tactile mapping logic 118 is configured to map sensed/calculated impedance values onto tactile feedback signals or commands. Mapping may include a function or lookup table, or may include a more complex algorithm and, if necessary, a finite state machine. Tactile mapping logic 118 determines what haptic effects are to be played and the order in which the effects are played in response to the sensed/calculated impedance values. Tactile mapping logic 118 outputs control signals to haptic feedback system 120 coupled to handle 102 to provide feedback information to an operator when performing a procedure. In general, high-level parameters that define a particular haptic effect include magnitude, frequency and duration. Low-level parameters such as pulse width modulation may also be used to determine a particular haptic effect.

In one embodiment, the formation of a transmural lesion may be associated with an impedance change of 10 ohms. A corresponding lookup table may be represented as follows:

| Impedance Change (ohm) | Haptic Amplitude (V) |
|---|---|
| 0 | 0 |
| 2 | 0 |
| 4 | 0 |
| 6 | 1 |
| 8 | 2.5 |
| 10 | 5 |

The above example is of a straightforward and non-complex lookup or function table to map sensed/calculated impedance values onto tactile feedback signals or commands provides increasing feedback to the surgeon as the lesion forms. Other lookup functions are possible and may be user-selectable and/or may be utilized to communicate other types of information to the user in the form of haptic effects. The other types of information that may be communicated include operating parameters of control system 112, such as but not limited to the frequency or power settings in the RF generator, as will be described in more detail herein.

Haptic feedback system 120 includes at least an actuator drive circuit 122 (shown in FIG. 2) which is coupled to a haptic actuator 124 (also shown as FIG. 2) for providing haptic feedback to the operator. In order to provide feedback to the operator, haptic feedback system 120 is electrically connected to control system 112. In one embodiment, in order to communicate commands from tactile mapping logic 118 to haptic actuator 124, impedance analyzer 116 provides a motor voltage along lead or tether 117 to handle 102 of tool 100. As such, tactile mapping logic 118 outputs control signals to drive circuit 122 which includes electronic components and circuitry used to supply haptic actuator 124 with the required electrical current and voltage to cause the desired haptic effects. As mentioned above, a fourth lead (not shown) may also be provided between control system 112 and handle 102 to provide an isolated ground line for a drive circuit 122 in handle 102 such that tactile mapping logic 118 communicates with haptic feedback system 120 via an isolated DC voltage line having two conductors. In one embodiment, haptic actuator 124 is a vibrotactile device that generates vibrations on handle 102 for haptic feedback. Other types of haptic feedback may be generated and provided to the user, including kinesthetic feedback (e.g., active and resistive force feedback), handle deformation, and/or other types of tactile feedback such as texture and heat. As shown in FIG. 1, multiple haptic actuators may be incorporated in handle 102 at several locations 119 for providing haptic effects to the fingers and thumb of a hand of the surgeon. Haptic actuators 124 may include electromagnetic motors, eccentric rotating mass ("ERM") actuators in which an eccentric mass is moved by a motor, linear resonant actuators ("LRAs") in which a mass attached to a spring is driven back and forth, shape memory alloys, electro-active polymers that deform in response to signals, mechanisms for changing stiffness, vibrotactile actuators, inertial actuators, piezoelectric actuators, or other suitable types of actuating devices. In one embodiment, haptic actuator 124 can be implemented as an inertial actuator to provide vibrotactile feedback to the operator. In another embodiment, kinesthetic haptic feedback may utilize, for example, solenoids to change the stiffness/damping of handle 102, small air bags that change size in handle 102, or shape changing materials. A detailed description of possibly haptic actuators suitable for use herein may be found in U.S. patent application Ser. No. 11/862,639, filed Sep. 28, 2007, herein incorporated by reference in its entirety.

In one embodiment, tactile feedback system 120 alerts the tool user of changes in tissue properties, i.e., when the impedance of the tissue indicates that the treatment procedure is complete. For example, haptic effects provided by tactile feedback system 120 may include a vibrotactile alert when the tissue has reached a target or predetermined impedance value and/or a kinesthetic barrier on the trigger of handle 102 as the impedance approaches the target impedance value.

In another embodiment, tactile feedback system 120 supplies information relating to the operating status of control system 112 to the user and/or may be utilized to control the behavior of the tool. For example, haptic effects provided by tactile feedback system 120 may provides information about the status of power source 114. For example, the frequency and amplitude settings of the RF generator/power source 114 may be mapped into a set of vibrotactile alerts to provide confirmation to the user that the generator is operating in a particular mode. As such, the surgeon would be able to "feel" that tool 100 is in the correct operating mode before engaging in electrosurgical activity. Further, the vibrotactile feedback may be varied or dynamic based on changing levels of frequency and amplitude of the RF generator during the surgical procedure. The variation of the vibrotactile feedback may be a change of amplitude, frequency, and/or duration.

In yet another embodiment, tactile mapping logic 118 may output command signals to power source 114. For example, when the impedance of the tissue indicates that ablation is complete, tactile mapping logic 118 may output a command signal to shut down power source 114, thereby preventing delivery of additional energy to the tissue and controlling the behavior of tool 100.

Referring to FIG. 3, an embodiment incorporating two types or modes of feedback for the operator is shown. Specifically, haptic feedback system 320 provides both haptic and audio feedback via haptic actuator 124 and an audio device or speaker 326. Tactile mapping logic 118 communicates the processed information to one or more of haptic actuator 124 and audio device 326 according to which ones of these feedback mechanisms are enabled and how they are controlled to provide their respective outputs.

In one embodiment, feedback may be provided to the operator in a continuous manner as the operator performs the surgery. In another embodiment, feedback may be provided to the operator as an alert to notify or warn the operator when a particular condition is satisfied. Further, one type of feedback may be provided in a continuous manner while another type of feedback is provided as an alert. For example, audio feedback may be provided to the operator in a continuous manner while haptic feedback is provided to the operator as an alert. Continuous audio feedback may inform the operator of the distance of measured/calculated impedance values and a haptic alert may be generated when the measured/calculated impedance values indicate that ablation is complete and transmural.

Referring to FIG. 4, an embodiment incorporating three types or modes of feedback for the operator is shown. Specifically, haptic feedback system 420 provides haptic, audio, and visual feedback via haptic actuator 124, audio device or speaker 326, and visual display 428, respectively. Tactile mapping logic 118 communicates the processed information to one or more of haptic actuator 124, audio device 326, visual display 428 according to which ones of these feedback mechanisms are enabled and how they are controlled to provide their respective outputs. In this embodiment, visual display 428 is a liquid crystal display (LCD) screen on a back region of handle 102. Visual display 428 may be used to display impedance information and/or the operating status of RF power source 114. In one embodiment, an ultrasound transducer (not shown) may be coupled to tip 108 of tool 100 and visual display 428 may be configured to show ultrasound image information to assist the surgeon to position the tool as needed. Visual display 428 can include a touch screen, which can be configured to present information to the operator and can also be configured to sense when the operator presses certain portions of the touch screen. In this way, the touch screen can act as a touchable user interface with graphical presentation capabilities. Visual display 428 may include a graphical user device that enables the surgeon to select different feedback profiles, adjust sensor behavior, modify supplemental information, and the like.

According to the embodiment of FIG. 4, handle portion 402 of surgical tool 400 may further include one or more buttons 432. Buttons 432 can be configured using any suitable mechanism for allowing an operator to control the nature of the feedback that is provided to the operator. Buttons 432 may include devices for allowing certain levels, intensities, or amplitudes to be adjusted or certain selections to be made regarding the output presented to the operator. In some embodiments, buttons 432 may be configured as switches, such as momentary toggle switches, allowing an operator to select different ways in which sensor information is mapped or provided to respective output devices. Buttons 432 can be implemented as a rocker switch or as a one-dimensional control surface. According to one function of buttons 432, the operator can enable or disable one or more output mechanisms by controlling whether or not output signals based on the sensed signals are provided to the respective output devices. Another function of buttons 432 includes the ability to enable one or more output mechanisms. In this regard, the operator can control if and how feedback is presented in a visual, auditory, and/or haptic fashion. With feedback tailored to the surgeon's preferences, the tool can provide feedback to supplement the operator experience for better operation and performance.

It will be apparent to those of ordinary skill in the art that embodiments hereof relate to any type of tools that can be manipulated by an operator. More particularly, the tools described in the present disclosure include a handle portion that mechanically controls a distal portion of the tool. According to embodiments hereof, a tissue contact element at a distal end of a device and a haptic feedback system may collectively function to extract impedance or pertinent information regarding the operating status of the control system that is subsequently communicated to the operator as haptic, audio, and/or visual feedback. Although embodiments disclosed are tools for laparoscopic surgery, other embodiments can be used for non-laparoscopic surgeries such as in vascular or other catheterization where information detected from a tissue contact element on the tool-tip can be communicated back to the catheter handle. Further, for endoscopy procedures, information detected from a tissue contact element on a flexible endoscope can be communicated back to the endoscope handle. Other embodiments can be used for telesurgery or telepresence in order to, for example, perform routine external examinations and/or utilize open surgical tools by a remote doctor.

While various embodiments according to the present invention have been described above, it should be understood that they have been presented by way of illustration and example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the appended claims and their equivalents. It will also be understood that each feature of each embodiment discussed herein, and of each reference cited herein, can be used in combination with the features of any other embodiment. All patents and publications discussed herein are incorporated by reference herein in their entirety.

What is claimed is:

1. A surgical tool comprising:
a handle;
an electrical tissue contact element operable to ablate tissue mounted on a distal portion of the tool, wherein the distal portion is connected to the handle via a shaft;
a power source electrically connected to the tissue contact element;
an impedance analyzer electrically connected to the tissue contact element, wherein the impedance analyzer receives impedance measurement signals from the tissue contact element and calculates tissue impedance;
a tactile mapping logic electrically connected to the impedance analyzer, wherein the tactile mapping logic receives calculated impedance information from the impedance analyzer and processes the information into signal commands; and
a feedback system including one or more haptic actuators coupled to the handle and electrically connected to the tactile mapping logic, wherein the tactile mapping logic communicates the signal commands to the feedback system and the feedback system uses the signal commands to generate a first haptic feedback relating to the calculated impedance information to the handle, and
wherein the feedback system separately communicates information to a user about operating parameters of the power source as a second haptic feedback generated by the feedback system, wherein the operating parameters include a frequency setting and an amplitude setting of the power source which are mapped into a set of vibrotactile alerts to provide confirmation that the power source is in a correct operating mode before the power source engages in electrosurgical activity and wherein at least one of an amplitude, a frequency, and a duration of the vibrotactile alerts vary based on changing levels of the operating parameters as the power source engages in electrosurgical activity, and
wherein the second haptic feedback is generated separate from the first haptic feedback.

2. The surgical tool of claim 1, wherein the haptic feedback generated by the feedback system informs a user of the formation of a transmural lesion.

3. The surgical tool of claim 2, wherein the formation of a transmural lesion is associated with a tissue impedance change of approximately 10 ohms.

4. The surgical tool of claim 2, wherein the feedback system generates a vibrotactile or kinesthetic alert upon the formation of a transmural lesion.

5. The surgical tool of claim 1, wherein the tactile mapping logic further communicates signal commands to the power source.

6. The surgical tool of claim 5, wherein the tactile mapping logic outputs a signal command to shut down the power source upon formation of a transmural lesion.

7. The surgical tool of claim 1, wherein the first and second haptic feedback generated by the feedback system each include at least one of vibratory feedback, kinesthetic feedback, texture feedback, and heat feedback.

8. The surgical tool of claim 1, wherein the feedback system uses the signal commands to further generate audio or visual feedback relating to the calculated impedance information.

9. The surgical tool of claim 1, wherein the feedback system is operable to provide feedback in a continuous manner.

10. The surgical tool of claim 1, wherein the feedback system is operable to provide feedback as an alert to notify the user when a particular condition is satisfied.

11. The surgical tool of claim 1, wherein the tissue contact element is a radiofrequency electrode and the power source is a radiofrequency generator.

12. The surgical tool of claim 1, wherein the power source, impedance analyzer, and tactile mapping logic are combined into an integral, external component that is spaced apart from the surgical tool.

13. The surgical tool of claim 1, wherein at least one of the power source, impedance analyzer, and tactile mapping logic are mounted within or on the handle.

14. The surgical tool of claim 1, wherein the tactile mapping logic utilizes a lookup table to process the calculated impedance information into signal commands.

15. The surgical tool of claim 1, wherein the tactile mapping logic utilizes an algorithm to process the calculated impedance information into signal commands.

16. A method of providing feedback to a user during an ablation surgical procedure, the method comprising the steps of:
monitoring impedance of tissue during the ablation surgical procedure via a radiofrequency electrode mounted on a distal portion of a surgical tool, wherein the surgical tool includes a power source electrically connected to the radiofrequency electrode;
processing the impedance information to determine the formation of a transmural lesion;
communicating a first haptic feedback to a handle of the surgical tool, wherein the first haptic feedback informs a user of the formation of a transmural lesion; and
separately communicating a second haptic feedback relating to operating parameters of the power source to the handle of the surgical tool, wherein the operating parameters include a frequency setting and an amplitude setting of the power source which are mapped into a set of vibrotactile alerts to provide confirmation that the power source is in a correct operating mode before the power source engages in electrosurgical activity and wherein at least one of an amplitude, a frequency, and a duration of the vibrotactile alerts vary based on changing levels of the operating parameters as the power source engages in electrosurgical activity.

17. The surgical tool of claim 16, wherein the first and second haptic feedback generated by the feedback system each include at least one of vibratory feedback, kinesthetic feedback, texture feedback, and heat feedback.

18. A surgical apparatus comprising:
a surgical tool having a tissue contact element mounted on a distal portion thereof, wherein the surgical tool includes a power source electrically connected to the tissue contact element;
a control system electrically connected to the tissue contact element, wherein the control system receives impedance measurement signals from the tissue contact element, calculates tissue impedance, and processes the calculated impedance information into signal commands; and
a feedback system including one or more haptic actuators coupled to a handle of the surgical tool and electrically connected to the control system, wherein the control system communicates the signal commands to the feedback system and the feedback system uses the signal commands to generate a first haptic feedback relating to the calculated impedance information to the handle, and
wherein the feedback system separately communicates information to a user about operating parameters of the power source as a second haptic feedback generated by the feedback system, wherein the operating parameters include a frequency setting and an amplitude setting of the power source which are mapped into a set of vibrotactile alerts to provide confirmation that the power source is in a correct operating mode before the power source engages in electrosurgical activity and wherein at least one of an amplitude, a frequency, and a duration of the vibrotactile alerts vary based on changing levels of the operating parameters as the power source engages in electrosurgical activity, and
wherein the second haptic feedback is generated separate from the first haptic feedback.

* * * * *